(12) United States Patent
Lourenco et al.

(10) Patent No.: US 12,391,636 B2
(45) Date of Patent: Aug. 19, 2025

(54) METHOD AND SYSTEM TO PRODUCE HYDROCARBON FEEDSTOCKS

(71) Applicants: 1304338 Alberta Ltd., Edmonton (CA);
1304342 Alberta Ltd., Edmonton (CA)

(72) Inventors: Jose Lourenco, Edmonton (CA);
MacKenzie Millar, Edmonton (CA)

(73) Assignees: 1304338 Alberta Ltd., Edmonton (CA);
1304342 Alberta Ltd., Edmonton (CA)

( * ) Notice: Subject to any disclaimer, the term of this patent is extended or adjusted under 35 U.S.C. 154(b) by 450 days.

(21) Appl. No.: 17/793,214

(22) PCT Filed: Jan. 5, 2021

(86) PCT No.: PCT/CA2021/050005
§ 371 (c)(1),
(2) Date: Jul. 15, 2022

(87) PCT Pub. No.: WO2021/146795
PCT Pub. Date: Jul. 29, 2021

(65) Prior Publication Data
US 2023/0064109 A1       Mar. 2, 2023

(30) Foreign Application Priority Data

Jan. 24, 2020   (CA) ................................ CA 3069717

(51) Int. Cl.
*C07C 29/151*     (2006.01)
*B01J 19/24*      (2006.01)
(Continued)

(52) U.S. Cl.
CPC ......... *C07C 29/1518* (2013.01); *B01J 19/245* (2013.01); *C01B 3/38* (2013.01);
(Continued)

(58) Field of Classification Search
CPC ...... C07C 29/1518; B01J 19/245; C01B 3/38; C01B 2203/0233; C01B 2203/0238;
(Continued)

(56) References Cited

U.S. PATENT DOCUMENTS 2,446,925 A    8/1948  Hemminger
2,495,613 A    1/1950  Tuttle
(Continued)

FOREIGN PATENT DOCUMENTS

CA       1098852      4/1981
CA       2691392      2/2007
(Continued)

OTHER PUBLICATIONS

International Search Report and Written Opinion mailed Apr. 13, 2021, issued in corresponding Application No. PCT/CA2021/050005, filed Jan. 5, 2021, 9 pages.
(Continued)

*Primary Examiner* — Jafar F Parsa
(74) *Attorney, Agent, or Firm* — CHRISTENSEN O'CONNOR JOHNSON KINDNESS PLLC (57) ABSTRACT

A method that combines a fuel cell with a Gas Recovery Unit (GRU) to a methanol plant to produce methanol at near zero GHG emissions. The fuel cell generates steam, carbon dioxide and electricity. A GRU unit condenses, separates, recovers, pressurizes and reheats the fuel cell anode exhaust stream. The GRU prepares a stream of natural gas and steam to feed the fuel cell anode and a stream of carbon dioxide and air to feed the fuel cell cathode. The GRU also prepares streams of carbon dioxide and steam as reactants for the stoichiometric mixture with natural gas to produce synthesis gas in an electric catalytic reformer at a methanol plant. The electric catalytic reformer uses electricity, steam and/or carbon dioxide reactants produced by the fuel cell to pro-
(Continued)

duce synthesis gas for conversion to methanol with low GHG emissions.

16 Claims, 3 Drawing Sheets

(51) Int. Cl.
    *C01B 3/38*            (2006.01)
    *H01M 8/0668*      (2016.01)

(52) U.S. Cl.
    CPC ... *H01M 8/0668* (2013.01); *C01B 2203/0233* (2013.01); *C01B 2203/0238* (2013.01); *C01B 2203/061* (2013.01); *C01B 2203/062* (2013.01); *C01B 2203/1241* (2013.01); *C01B 2203/84* (2013.01)

(58) Field of Classification Search
    CPC ........ C01B 2203/061; C01B 2203/062; C01B 2203/1241; C01B 2203/84; H01M 8/0668
    See application file for complete search history.

(56) References Cited

U.S. PATENT DOCUMENTS

| | | | |
|---|---|---|---|
| 4,094,767 | A | 6/1978 | Gifford |
| 4,187,672 | A | 2/1980 | Rasor |
| 4,213,826 | A | 7/1980 | Eddinger et al. |
| 4,265,736 | A | 5/1981 | Thayer |
| 4,306,961 | A | 12/1981 | Taciuk |
| 4,323,446 | A | 4/1982 | Chervenak et al. |
| 4,404,086 | A | 9/1983 | Oltrogge |
| 4,459,201 | A | 7/1984 | Eakman et al. |
| 4,561,966 | A | 12/1985 | Owen et al. |
| 5,014,785 | A | 5/1991 | Puri et al. |
| 5,039,579 | A | 8/1991 | Kinoshita |
| 5,084,362 | A | 1/1992 | Farooque |
| 5,085,274 | A | 2/1992 | Puri et al. |
| 5,133,406 | A | 7/1992 | Puri |
| 5,232,793 | A | 8/1993 | Miyauchi et al. |
| 5,332,036 | A | 7/1994 | Shirley et al. |
| 5,402,847 | A | 4/1995 | Wilson et al. |
| 5,422,195 | A | 6/1995 | Bernard |
| 5,536,488 | A | 7/1996 | Mansour et al. |
| 6,187,465 | B1 | 2/2001 | Galloway |
| 6,432,565 | B1 | 8/2002 | Haines |
| 7,459,226 | B2 | 12/2008 | Huijsmans |
| 7,550,063 | B2 | 6/2009 | Gawad |
| 7,753,972 | B2 | 7/2010 | Zubrin et al. |
| 7,946,346 | B2 | 5/2011 | Zornes |
| 8,088,528 | B2 | 1/2012 | Lourenco et al. |
| 8,349,504 | B1 | 1/2013 | Radovich |
| 8,585,891 | B2 | 11/2013 | Lourenco et al. |
| 8,616,294 | B2 | 12/2013 | Zubrin et al. |
| 9,077,005 | B2 | 7/2015 | Berlowitz et al. |
| 9,132,415 | B2 | 9/2015 | Lourenco et al. |
| 9,605,523 | B2 | 3/2017 | Zubrin et al. |
| 10,014,541 | B2 | 7/2018 | Jamal et al. |
| 10,787,891 | B2 | 9/2020 | Millar et al. |
| 10,968,725 | B2 | 4/2021 | Lourenco et al. |
| 2003/0022035 | A1 | 1/2003 | Galloway |
| 2004/0115492 | A1 | 6/2004 | Galloway |
| 2004/0229102 | A1 | 11/2004 | Jahnke et al. |
| 2005/0022695 | A1 | 2/2005 | Abatzoglou et al. |
| 2005/0220695 | A1 | 10/2005 | Abatzoglou et al. |
| 2005/0271914 | A1 | 12/2005 | Farooque et al. |
| 2006/0159967 | A1 | 7/2006 | Huijsmans et al. |
| 2007/0099038 | A1 | 5/2007 | Galloway |
| 2008/0296018 | A1 | 12/2008 | Zubrin et al. |
| 2009/0155637 | A1 | 6/2009 | Cui et al. |
| 2010/0021619 | A1 | 1/2010 | Fujihara et al. |
| 2010/0163226 | A1 | 7/2010 | Zornes |
| 2010/0215566 | A1 | 8/2010 | Lourenco et al. |
| 2010/0261938 | A1 | 10/2010 | Olah et al. |
| 2011/0094940 | A1 | 4/2011 | Weisselberg |
| 2011/0163011 | A1 | 7/2011 | Yarbro |
| 2011/0206571 | A1 | 8/2011 | Skinner et al. |
| 2011/0207002 | A1 | 8/2011 | Powell et al. |
| 2012/0251898 | A1 | 10/2012 | Lehar et al. |
| 2012/0251899 | A1 | 10/2012 | Lehar et al. |
| 2013/0118735 | A1 | 5/2013 | Jamal et al. |
| 2013/0260268 | A1 | 10/2013 | Shapiro et al. |
| 2014/0272617 | A1 | 9/2014 | Berlowitz et al. |
| 2014/0272638 | A1 | 9/2014 | Berlowitz et al. |
| 2014/0272734 | A1 | 9/2014 | Braun et al. |
| 2014/0338901 | A1 | 11/2014 | Sites et al. |
| 2015/0188172 | A1 | 7/2015 | Yun et al. |
| 2015/0361833 | A1 | 12/2015 | Hinders et al. |
| 2016/0130513 | A1 | 5/2016 | Galloway |
| 2016/0351930 | A1 | 12/2016 | Jahnke et al. |
| 2017/0271701 | A1* | 9/2017 | Berlowitz ......... H01M 8/04805 |

FOREIGN PATENT DOCUMENTS

| | | |
|---|---|---|
| CA | 2641747 | 10/2008 |
| CA | 2515999 | 12/2012 |
| CA | 2690836 | 2/2016 |
| CA | 2920656 | 3/2018 |
| CL | 202100663 | 7/2021 |
| CN | 101498229 | 1/2008 |
| CN | 102937016 | 2/2013 |
| GB | 977905 | 12/1964 |
| GB | 2471862 | 1/2011 |
| JP | 04034861 | 2/1992 |
| JP | 3038393 | 5/2000 |
| JP | 2003095615 | 4/2003 |
| JP | 2006104261 | 4/2006 |
| JP | 2010-15860 | 1/2010 |
| JP | 2012233534 | 11/2012 |
| JP | 2015-502639 | 1/2015 |
| WO | 1999/10945 | 3/1999 |
| WO | 2005/001977 | 1/2005 |
| WO | 2010/058750 | 5/2010 |
| WO | 2010/115283 | 10/2010 |
| WO | 2011/081665 | 7/2011 |
| WO | 2012/000115 | 1/2012 |
| WO | 2012/092404 | 7/2012 |
| WO | 2013/074875 | 5/2013 |
| WO | 2014/138208 | 9/2014 |
| WO | 2015/059507 | 4/2015 |
| WO | 2015/106820 | 7/2015 |
| WO | 2017/059515 | 4/2017 |
| WO | 2017/059516 | 4/2017 |
| WO | 2017/096467 | 6/2017 |
| WO | 2017/132773 | 8/2017 |
| WO | 2017/189785 | 11/2017 |
| WO | 2018/044913 | 3/2018 |
| WO | 2019/169475 A1 | 9/2019 |

OTHER PUBLICATIONS

International Search Report mailed Aug. 26, 2010, issued in International Application No. PCT/CA2010/000530, filed Apr. 7, 2010, 3 pages.
International Search Report mailed Oct. 31, 2011, issued in International Application No. PCT/CA2011/050403, filed Jun. 30, 2011, 3 pages.
International Search Report and Written Opinion mailed Feb. 24, 2014, issued in International Application No. PCT/CA2013/050955, filed Dec. 12, 2013, 7 pages.
International Search Report and Written Opinion mailed Jun. 20, 2016, issued in International Application No. PCT/CA2015/051022, filed Oct. 8, 2015, 7 pages.
Jacobs Consultancy, "Evaluation of Integrating a Molten Carbonate Fuel Cell (MCFC) With a SADG Facility," prepared for Alberta Innovates—Energy and Environment Solutions, Jul. 2015, 77 pages.
International Search Report and Written Opinion mailed Feb. 21, 2017, issued in International Application No. PCT/CA2016/051408, filed Dec. 1, 2016, 9 pages.
Hisato, A., "Upgrading of Heavy Crude Oil—Supercritical Water (56) References Cited

OTHER PUBLICATIONS

Cracking Technology," JOGMEC Techno Forum 2014, Nov. 26-27, 2014, 27 pages.

Hill, R., et al., "Application of Molten Carbonate Fuel Cell for CO2 Capture in Thermal In Situ Oil Sands Facilities," International Journal of Greenhouse Gas Control 41:276-284, 2015.

Hamelinck, C.N., et al., "Potential for CO2 Sequestration and Enhanced Coalbed Methane Production in the Netherlands," NOVEM Programme No. 234.1, Mar. 2001 (ISBN 90-5847-020-4), 105 pages.

International Search Report and Written Opinion mailed Apr. 18, 2019, issued in corresponding International Application No. PCT/CA2019/050159, filed Feb. 7, 2019, 16 pages.

International Search Report and Written Opinion mailed Mar. 27, 2017, issued in International Application No. PCT/CA2017/050062, filed Jan. 20, 2017, 7 pages.

International Search Report and Written Opinion mailed Apr. 7, 2021, issued in International Application No. PCT/CA2021/050005, filed Jan. 5, 2021, 9 pages.

International Search Report and Written Opinion mailed May 31, 2016, issued International Application No. PCT/CA2015/051136, filed Nov. 4, 2015, 13 pages.

\* cited by examiner

METHOD AND SYSTEM TO PRODUCE HYDROCARBON FEEDSTOCKS

FIELD

This relates to a method of producing hydrocarbon feedstocks, and in particular, a method that produces hydrocarbon feedstocks using natural gas and the exhaust streams from a fuel cell.

BACKGROUND

Methanol is a large volume commodity chemical. The production of methanol is well understood as an energy intensive catalytic process that first produces a synthesis gas for a catalytic methanol synthesis reactor. Industrially, methanol is produced mainly by indirect liquefaction of natural gas. The indirect liquefaction process is generally done in two steps: catalytic reforming of natural gas into synthesis gas, followed by catalytic methanol synthesis conversion into methanol. The three main routes to convert natural gas into synthesis gas are steam reforming (SMR), partial oxidation (PDX) and auto thermal reforming (ATR). The most widely used technology in the industry to produce synthesis gas for methanol synthesis is steam reforming. Auto thermal reforming has gained more prominence in the industry of late due to an increase in efficiencies. Another improvement to the methanol production plants is the addition of carbon dioxide into the steam/natural gas mixed stream before the steam reforming reactor to change the ratio of hydrogen to carbon monoxide in the produced synthesis gas from 3:1 to 2:1. A synthesis gas with a hydrogen to carbon monoxide ratio of 2:1 is the ideal stoichiometric ratio for the production of methanol. Another improvement to convert natural gas into synthesis gas is the replacement of natural gas fired furnaces with electric furnaces. This development reduces greenhouse gas (GHG) emissions, particularly when electricity is provided by a green power generation source such as wind or solar.

PCT patent publication no. WO 2017/059516 (Millar et al.) entitled "Producing pressurized and heated fluids using a fuel cell" and WO2017/136920 (Lourenco et al.) entitled "Method of extracting coal bed methane using carbon dioxide" describe the recovery of carbon dioxide and water from a fuel cell, and using these components to enhance hydrocarbon production, such as solvents and thermal energy suppliers.

SUMMARY

According to an aspect, there is provided a method of producing methanol that combines a fuel cell that requires two inputs: natural gas and air, typically atmospheric air. The fuel cell generates electricity, steam and carbon dioxide that may be used to feed a methanol production process. In particular, the method permits the recovery of the fuel cell anode exhaust stream components of water, carbon dioxide, and thermal energy. These components may be condensed, separated, recovered, pressurized and reheated to produce carbon dioxide and steam from the fuel cell anode exhaust stream that may then be delivered at high pressure and high temperature to be mixed with natural gas at the stoichiometric ratio for conversion into synthesis gas in an electric furnace.

According to an aspect, the method uses natural gas and atmospheric air to feed an electricity generator fuel cell, which produces electricity, steam and carbon dioxide as exhaust streams. The method recovers water, carbon dioxide and thermal energy from the anode exhaust stream, then mixes the recovered streams with natural gas at a stoichiometric ratio to feed an electric catalytic reactor to produce synthesis gas for conversion into methanol in a methanol synthesis reactor. The electricity provides energy for an electric catalytic furnace to convert the fuel cell produced steam and carbon dioxide with methane added at a stoichiometric ratio to produce synthesis gas for conversion into hydrocarbon feedstocks in a synthesis reactor, such as methanol in a methanol synthesis reactor, at near zero GHG emissions.

According to another aspect, the method may permit the generation of electricity by the fuel cell at near zero GHG emissions to supply the methanol plant. The method may also permit the recovery of thermal energy in the methanol process to produce more electricity through Rankine Cycle power generators, such as ORC's (Organic Rankine Cycle) for plant use, which may be used to further reduce the overall plant energy requirements and improve the overall efficiency. The method thus permits the use of a fossil fuel (natural gas) to produce a major petrochemical feedstock (methanol) at near zero GHG emissions.

According to an aspect, the method may be used to enhance the efficiency of producing methanol by combining a fuel cell and a Gas Recovery Unit (GRU) with a methanol plant that uses an electric furnace for the catalytic production of synthesis gas and conversion to methanol in a methanol synthesis reactor. The method may be used to produce methanol at near zero GHG emissions.

The process of generating power with a natural gas fuel cell differs from standard power generation plants that use natural gas. In a fuel cell, natural gas is consumed at the anode through an electrochemical reaction that produces electricity and a hot exhaust stream of gases, mainly steam and carbon dioxide, whereas in combustion based power generation plants the exhaust stream is mainly nitrogen and nitrogen oxides with water vapor and carbon dioxide being minor components by mass or volume in the combustion exhaust stream. The fuel cell may be any suitable type of fuel cell, such as molten carbonate, solid oxide, etc. The fuel cell anode exhaust stream is mainly carbon dioxide and water vapor, which combined is less than 75% of the exhaust mass flow rate of a power generation combustion process. The concentrated fuel cell anode exhaust stream with its thermal energy is an ideal source to recover and convert steam and carbon dioxide into reactants for the production of methanol. The anode exhaust stream is a byproduct of producing electricity with a fuel cell. Typically, the thermal energy of this anode exhaust gas stream is exhausted into the atmosphere or partially recovered in cogeneration processes as a source of thermal heat before the exhaust gas is released into the atmosphere.

According to an aspect, the method may have one or more of the following features:
  Power generation by chemical reaction of natural gas with air, such as atmospheric air, in a fuel cell.
  Low or zero GHG emissions released into the atmosphere as the fuel cell anode exhaust stream mixture of carbon dioxide and water, and its thermal energy are recovered in a GRU and supplied as reactants to a methanol plant.
  The fuel cell acts as an energy provider (thermal+electrical) and a producer of high-quality reactant streams of carbon dioxide and steam.
  An electric furnace at the methanol plant converts the mixture of fuel cell-produced reactants and natural gas at the stoichiometric ratio to catalytically produce a synthesis gas at hydrogen to carbon monoxide ratio of 2:1 for the methanol synthesis conversion into methanol.

The recovery of thermal energy in the methanol plant produces electricity via Rankine Cycle plants, such as Organic Rankine Cycle (ORC) plants.

According to an aspect, there is provided a method of producing electricity for internal use and/or export from a fuel cell, such as a molten carbonate fuel cell. A GRU cools, condenses, separates, recovers, pressurizes and reheats the fuel cell exhaust streams for internal use in the method and for export as reactants to a methanol unit. The GRU also treats the natural gas to supply the fuel cell and the methanol plant.

According to other aspects, the method first recovers water, carbon dioxide and thermal energy from an electricity generator fuel cell high temperature anode exhaust stream, then mixes it with GRU-treated natural gas at a stoichiometric ratio to feed an electric furnace that produces synthesis gas at a hydrogen to carbon monoxide ratio of 2:1 for methanol synthesis conversion into methanol. This method uses natural gas and atmospheric air as feedstocks to a GRU that prepares feed streams for a fuel cell and a methanol plant.

According to some aspects, the above method may operate at any site where natural gas is available. The electric furnace energy may be delivered by various sources, such as a heated outside catalytic tube wall, a heating element immersed inside the catalytic tube, a heating element coated with a catalyst formulation, or heating elements immersed in catalytic micro-channel reactors. The thermal heat recovery in the methanol plant may be done through ORCs to generate electricity, compared with the current practice of steam generation and cooling water heat exchange. This method may also be applicable to processes that convert synthesis gases into products other than methanol.

According to an aspect, there is provided a method to produce methanol by mixing natural gas with cooled, condensed, separated, recovered, pressurized and reheated carbon dioxide and steam from a high temperature fuel cell anode exhaust stream. The method includes providing a supply of natural gas to a GRU for treatment to supply a fuel cell and a methanol plant. First, a supply of pipeline natural gas is routed to a GRU for gas treatment, heated, mixed with heated recovered steam, and supplied to the fuel cell anode. A supply of atmospheric air is also routed to the GRU and is mixed with recovered carbon dioxide and heated to supply the fuel cell cathode. In the anode of the fuel cell, the GRU-treated natural gas stream may be steam reformed to produce hydrogen and carbon dioxide, and the hydrogen may be further reacted with a carbonate ion to produce steam, carbon dioxide and electricity. The anode-produced steam and carbon dioxide exit the anode as a high temperature exhaust gas stream to the GRU. At the GRU, the anode exhaust stream is cooled, condensed, recovered, separated, pressurized and heated for re-use in the fuel cell anode and export to the methanol unit. The cathode exhaust stream, mainly nitrogen, exits the fuel cell and may also enter the GRU, where it is cooled and recovered for other uses or released into the atmosphere. The objective of the GRU is to treat the fuel cell inlet streams and to recover and prepare the fuel cell outlet streams for re-use and export. In this proposed method, the GRU exports steam, carbon dioxide and treated natural gas as reactants to a methanol unit, where the GRU treated natural gas is mixed with recovered steam and carbon dioxide at the stoichiometric ratio to produce a synthesis gas with a hydrogen to carbon monoxide ratio of 2:1 in an electric catalytic reformer. The produced synthesis gas is then fed to a methanol synthesis reactor for conversion into methanol. The fuel cell provides electricity to an electric furnace for the catalytic conversion of the mixed treated natural gas, steam and carbon dioxide into synthesis gas. The method may be used to produce methanol at near zero GHG emissions.

According to an aspect, there is provided a method of producing synthesis gas using a fuel cell having an anode and a cathode, a Gas Recovery Unit (GRU), and an electric catalytic reformer. The method comprises the steps of: operating the fuel cell to generate electricity and an exhaust stream comprising steam and carbon dioxide, the fuel cell being connected to a power distributor; using the GRU, conditioning and separating the exhaust stream to produce streams of steam and carbon dioxide; producing a reformer input stream by combining a stream of methane, the stream of carbon dioxide, and the stream of steam according to a stoichiometric ratio required to produce a stream of synthesis gas; reacting the reformer input stream in the electric catalytic reformer to produce the stream of synthesis gas, the electric catalytic reformer being powered by the power distributor; and using a power generator, recovering heat from the stream of synthesis gas to produce electricity, the power generator being connected to the power distributor.

According to other aspects, the method may comprise one or more of the following steps, alone or in combination: the stream of synthesis gas may be reacted in a synthesis reactor to produce a petrochemical; heat may be recovered from the synthesis reactor using a power generator, such as a Rankine Cycle or an Organic Rankine Cycle, that is connected to the power distributor; the GRU may receive a natural gas stream, and may condition a first portion of the natural gas stream as a fuel gas stream to feed the fuel cell anode, and a second portion of the natural gas stream as the stream of methane, and the GRU may further condition a fuel stream of steam that is mixed with the fuel gas stream to feed the anode of the fuel cell; the stoichiometric ratio of methane, carbon dioxide, and steam may be 3:1:2, and the method may further comprise the step of reacting the synthesis gas in a methanol synthesis reactor to produce methanol, and the method may further comprise the step of recovering heat from the methanol synthesis reactor using a power generator to produce electricity, the reactor power generator, which may be a Rankine Cycle or an Organic Rankine Cycle, may be connected to the power distributor.

According to an aspect, there is provided a system for producing hydrocarbon-based products, the system comprises a power distributor, and a fuel cell having an anode and a cathode, the fuel cell generating electricity and an exhaust stream comprising steam and carbon dioxide, the power distributor receiving electricity from the fuel cell. A Gas Recovery Unit (GRU) is connected to the fuel cell. The GRU is adapted to condition an input stream of natural gas to produce a first methane stream and a second methane stream, the first methane stream comprising fuel gas for the fuel cell; condition the exhaust stream from the fuel cell to produce a stream of steam and a stream of carbon dioxide; and control an output of the second methane stream, the stream of steam and the stream of carbon dioxide according to a stoichiometric ratio. An electric catalytic reformer receives the second methane stream, the stream of steam, and the stream of carbon dioxide. The electric catalytic reformer is powered by electricity from the power distributor to produce a stream of synthesis gas. A power generator that recovers heat from the stream of synthesis gas to produce electricity. The power generator is connected to the power distributor.

According to other aspects, the system may comprise one or more of the following aspects, alone or in combination: there may be a synthesis reactor that reacts the stream of synthesis gas to produce a petrochemical, such as methanol, in an exothermic reaction, and there may further be a power generator, such as a Rankine Cycle or an Organic Rankine Cycle, that generates electricity from heat produced by the synthesis reactor where the power generator is connected to the power distributor; the stoichiometric ratio of methane, carbon dioxide and steam may be 3:1:2; the GRU may be adapted to mix a portion of steam obtained from the exhaust stream with the first methane stream as a fuel stream for the anode of the fuel cell.

According to an aspect, there is provided a method of producing methanol using a fuel cell, a Gas Recovery Unit (GRU), and a methanol plant. The fuel cell is operated to generate electricity and an exhaust stream comprising steam and carbon dioxide. The exhaust stream is received from the fuel cell at the GRU, and the GRU unit conditions the exhaust stream to produce a steam stream and a carbon dioxide stream. The GRU also conditions an input stream of natural gas to mix with the GRU-treated natural gas to be reacted in an electric catalytic reformer to produce synthesis gas for conversion to methanol in a methanol synthesis reactor. The fuel cell is a generator of steam and carbon dioxide reactants and electricity for the electric catalytic reactor to produce methanol at near zero GHG emissions. The method comprises the steps of: providing a pressurized natural gas supply stream to a GRU and to a methanol unit; providing an air supply stream to a GRU; providing a fuel cell for power generation fueled by natural gas; and providing a methanol unit with an electric catalytic reformer and a methanol synthesis unit.

According to other aspects, the method may further comprise one or more of the following aspects, alone or in combination: the GRU unit may be employed to prepare a stream of steam to mix with natural gas and feed the fuel cell anode; the GRU unit may be employed to prepare a stream of carbon dioxide to mix with air and feed the fuel cell cathode; the GRU unit may be employed to condense separate, pressurize and reheat the fuel cell anode exhaust stream as reactants streams for a methanol unit; the GRU unit may be employed to condition the natural gas stream supply to a methanol unit; the fuel cell may provide GHG emissions free electricity to a methanol unit; reactant steam and reactant carbon dioxide together with electricity may be generated in a fuel cell and delivered to an electric catalytic reactor at a methanol unit; the heat recovery of synthesis gas may be done through an ORC to generate electricity; heat removal in the methanol synthesis reactor may be done through an ORC to generate electricity; the heat recovery of methanol synthesis gas stream may be done through an ORC to generate electricity; the natural gas supply may be liquid natural gas (LNG) in lieu of a pressurized natural gas supply; the proposed process may be located at any natural gas supply infrastructure; the method may produce methanol at near zero GHG emissions; wherein the fuel cell produces steam, carbon dioxide and electricity at near zero GHG emissions and a GRU prepares and delivers steam and carbon dioxide as reactants for processes other than methanol; the fuel cell may be operated to produce a desired amount of steam and carbon dioxide, and any excess electricity may be sold to a third-party consumer.

BRIEF DESCRIPTION OF THE DRAWINGS

These and other features will become more apparent from the following description in which reference is made to the appended drawings. The drawings are for the purpose of illustration only and are not intended to in any way limit the scope of the invention to the particular embodiment or embodiments shown, wherein.

DETAILED DESCRIPTION OF THE PREFERRED EMBODIMENT

Figure 1:
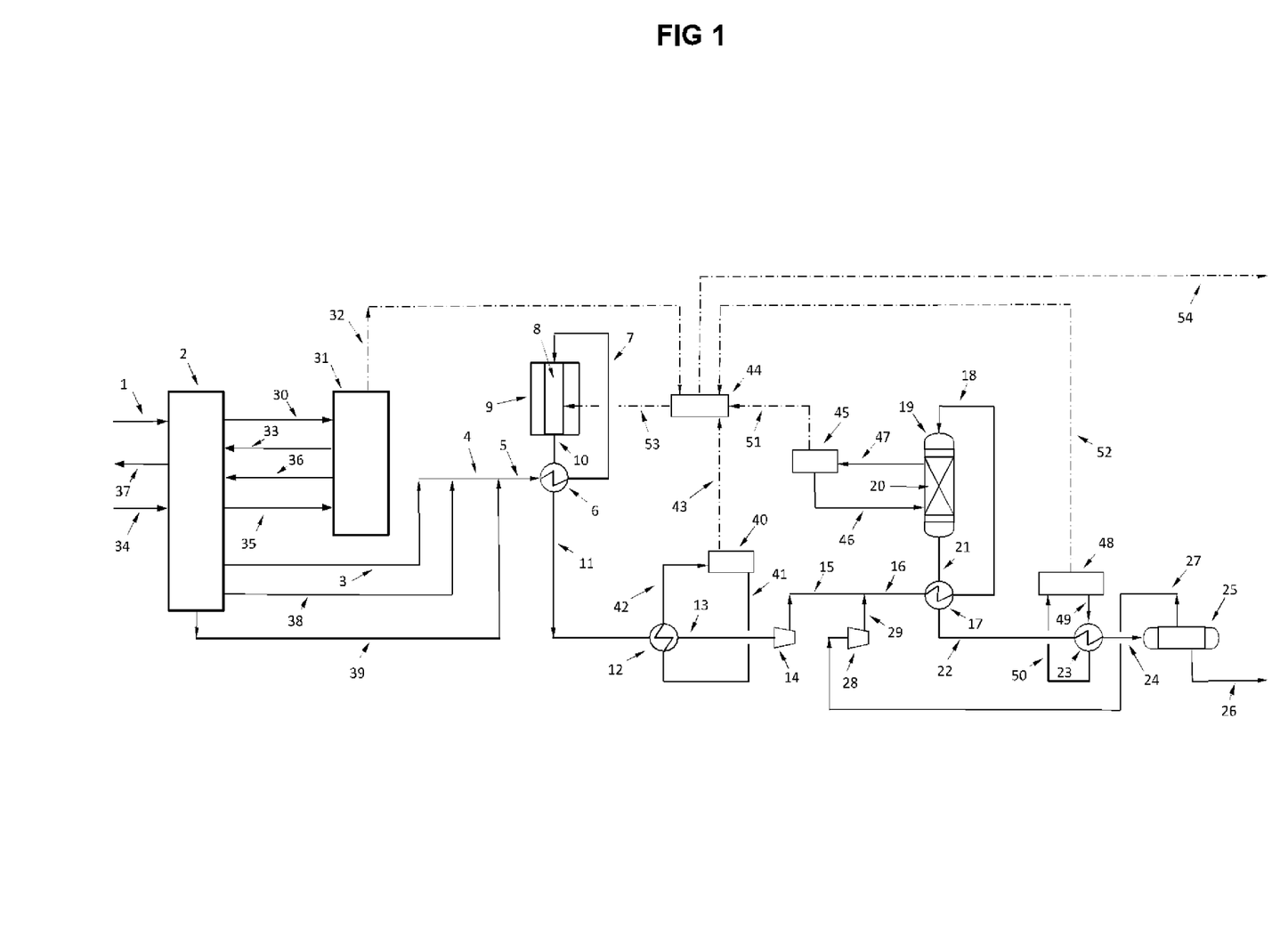
FIG. 1 is a process flow diagram of the preferred method to produce methanol.

Referring to FIG. 1, there is shown a method that may be used to produce methanol or other petrochemicals at zero or near zero greenhouse gas (GHG) emissions. As the depicted flow diagram is designed to produce methanol, the discussion below will be given primarily in the context of methanol production.

The depicted method combines a fuel cell unit 31 and a Gas Recovery Unit (GRU) 2 with a methanol plant using an electric catalytic reformer 8. The method has two inputs: natural gas 1 and atmospheric air 34 to generate methanol 26 at near zero GHG emissions. As described herein, natural gas is described as the input stream into GRU 2, and methane may be described as the output that is used as fuel for the fuel cell and for generating the synthesis gas. It will be understood that natural gas as used in the industry is primarily made up of methane, although there may be a small fraction of heavier hydrocarbons within the stream of natural gas. While not discussed herein, GRU 2 may include components that allow heavier hydrocarbons to be extracted from the stream of natural gas, as known in the art, and in order to provide methane at a sufficient quality for the intended purposes. This may not be required if the input stream of natural gas is of sufficient quality when received, in which case GRU 2 may be used to condition the natural gas for use in generating synthesis gas or to fuel the fuel cell 31. While fuel cells 31 are typically operated to satisfy demand for electrical power, when used as part of a methanol plant, fuel cell 31 may be operated to generate the reactants required for methanol production as described herein and electricity may be considered a byproduct.

The fuel cell 31 generates electricity 32 and produces a concentrated stream 33 of carbon dioxide and water that exits the fuel cell anode, generally at temperatures greater than 600 Celsius. The high temperature, high concentration stream 33 of carbon dioxide and water is cooled, separated, recovered, pressurized and reheated by the heat in the exhaust stream and mixed with natural gas treated by the GRU 2 to supply an electric catalytic reformer 8 to produce a stream 11 of synthesis gases for conversion into methanol. The fuel cell may be operated such that the anode exhaust stream provides the exact stoichiometric ratio of carbon dioxide to water as required for methanol production, as the ratio of carbon dioxide produced to water is 2 moles of water per mole of carbon dioxide, and production of methanol by stoichiometry requires 3 $CH_4 + CO_2 + 2H_2O \rightarrow 4CH_3OH$. By adding 3 moles of methane (the primary component of natural gas) per mole of carbon dioxide and 2 moles of water as recovered, prepared and delivered by the GRU, 4 moles of methanol may be produced. In addition, the electricity generated by the fuel cell may be used to provide the energy source for the endothermic reaction that occurs in the electric catalytic reactor 8 at the methanol plant. In this manner, the exhaust from the fuel cell may be captured and used to prevent the emission of GHG to the atmosphere. In particular, the anode exhaust stream may be cooled, condensed, separated, recovered, pressurized and reheated by the high temperature of the anode exhaust stream and supplied as reactants to a methanol processing unit. Thus the fuel cell generates electricity and produces high temperature, high pressure reactants for the production of methanol in an electric catalytic reactor at near zero GHG emissions.

The preferred fuel cell is a molten carbonate fuel cell, simply because they have been in commercial operation for over 20 years with plant sizes ranging from 300 KW to 59 MW, hence able to meet any industrial needs. Fuel cells such as the Direct Fuel Cell (DFC) manufactured by Fuel Cell Energy in the USA have been available since 2003. The largest DFC power generation plant is a 59 MW built in South Korea. Other fuel cells such as solid oxide fuel cells may also be used to supply the steam and carbon dioxide to electric catalytic reactors in methanol plants, however commercial size units in the MW range are not commercially available. When available in the future, due to its high temperature operation and higher efficiencies over the molten carbonate fuel cell, the solid oxide fuel cell will be able to further improve efficiencies in the production of methanol as proposed herein.

In the example depicted in FIG. 1, a natural gas stream 1 from a pipeline is routed to Gas Recovery Unit (GRU) 2 where it is split into stream 3, intended for the catalytic reformer 8, and stream 30, intended for the fuel cell 31. Within GRU 2, each stream is treated to operational parameters required for catalytic reformer 8 and fuel cell 31, respectively. It will be understood that GRU 2 may not be a single unit, but instead may be considered a number of different components used to achieve a desired pressure and temperature, remove condensates or contaminants, separate other components, etc. from the streams passing through GRU 2. As those skilled in the art are familiar with various processes and equipment that may be used to conditions the streams described herein, no further discussion will be given.

After exiting GRU 2, the treated, pressurized, and heated natural gas stream 3 is mixed with steam generated at the GRU 2, through stream 38, at a ratio that complies with the desired stoichiometric ratio. The stoichiometric mixed natural gas and steam stream 4 is further mixed with carbon dioxide produced in GRU 2, through stream 39 at a ratio that complies with the desired stoichiometric ratio. The stoichiometric mixture of natural gas, steam and carbon dioxide stream 5 may be further heated in heat exchanger 6 by the synthesis gas stream 10 exiting the catalytic reformer 8 in electric furnace 9. The heated mixture stream 7 enters catalytic reformer 8 in electric furnace 9 where the mixture stream is converted into synthesis gas at a hydrogen to carbon monoxide ratio of 2:1 in an endothermic reaction. The produced synthesis gas exits the catalytic reformer 8 through stream 10 and is cooled in heat exchanger 6. The pre-cooled synthesis gas stream 11 is further cooled in heat exchanger 12 by a closed loop Organic Rankine Cycle (ORC) unit 40, or other suitable generator that is capable of converting heat to electrical energy. The cooled stream 13 enters compressor 14 and is pressurized to meet methanol synthesis reactor 19 operating pressure. The pressurized synthesis gas stream 15 is mixed with a recycled stream 29 of unreacted synthesis gas separated from produced methanol in separator 25. The mixed synthesis and recycle gas stream 16 is heated in heat exchanger 17 and fed through stream 18 into methanol synthesis reactor 19. The synthesis gas is distributed into catalytic bed 20 where the synthesis gas is converted into methanol by an exothermic reaction. Heat is continuously removed from the catalytic reactor by a closed loop ORC unit 45 to control the temperature of the reaction. A mixture of produced methanol and unreacted synthesis gas exits methanol synthesis reactor 19 through stream 21 and is cooled by heat exchanger 17. The pre-cooled stream 22 is further cooled in heat exchanger 23 by a closed loop ORC unit 48. The cooled stream 24 enters separator 25 where the produced methanol is separated and exits through stream 26 to feed a methanol distillation unit. The separated unreacted synthesis gas exits through stream 27 and enters recycle compressor 28 to produce the recycled pressurized synthesis gas stream 29, which is mixed with synthesis gas stream 15 and fed to methanol reactor 19.

Referring again to GRU 2, in the depicted example, the inlet stream 1 of natural gas and the inlet stream 34 of atmospheric air are the only two inputs to the fuel cell/GRU/methanol plant process. At the GRU 2, stream 30 is produced to feed the anode in fuel cell 31. Stream 30 is a stoichiometric mixture of natural gas and steam. The steam mixed with natural gas in stream 30 was recovered and prepared in the GRU from stream 33. Stream 33, the anode exhaust stream, is a high temperature concentrated stream of carbon dioxide and steam. A portion of the recovered steam is prepared to be added to stream 30. Stream 35 is produced at the GRU 2 to feed the cathode of fuel cell 31. Stream 35 is a stoichiometric mixture of atmospheric air, supplied by stream 34 and recovered carbon dioxide from stream 33. The cathode exhaust stream 36 from fuel cell 31 is comprised mainly of nitrogen. Cathode exhaust stream 36 may be conditioned by GRU 2, such as to recover thermal energy carried by exhaust stream 36, and exits as stream 37 for other potential uses or is released into the atmosphere. A portion of the steam recovered from stream 33 is pressurized and heated as stream 38, exiting GRU 2 and added, at a stoichiometric ratio, to GRU-treated natural gas stream 3. A portion of the carbon dioxide recovered from stream 33 is pressurized and heated as stream 39 and added at a stoichiometric ratio to the natural gas/steam mixed stream 4. It will be understood that the stoichiometric ratio will be selected based on the petrochemical to be produced. As can be seen based on the discussion herein, the exhaust stream of fuel cell 31 is suitable for methanol based on the ratio of steam and carbon dioxide that is produced, although the amounts may be controlled or supplemented to any desired ratio.

A feature of the process described herein is the thermal energy recovery of certain process streams, such as streams 11, 22 and catalytic reactor 19 by ORC units 40, 45 and 48. These units convert the recovered thermal energy into electricity. The current mode of thermal recovery operation in existing methanol units is to produce steam to meet the needs of the catalytic reformer. In the depicted methanol process, the steam is produced by fuel cell 31 and prepared by GRU 2. Hence the thermal energy produced in the methanol plant is available to be recovered by ORC units to generate electricity for export and use in the methanol unit. The electricity generated in ORC units 40, 45 and 48 is routed to a Motor Control Centre (MCC) building 44 through electrical lines 43, 51, 52 along with electrical line 32 from fuel cell 31. Electrical line 53 delivers power from MCC 44 to electrical furnace 9. Any excess electricity available is exported through electrical line 54 to a third-party consumer. MCC 44 may also be referred to as a power distributor. While MCC 44 is shown as being a centralized unit, it will be understood that the various components that make up MCC 44 may be distributed to among various components. The various components will generally be controlled by, or monitored by, a central processing unit to ensure all elements that are powered by MCC 44 receive the demanded power.

In one example, the exhaust from a fuel cell, such as the steam, carbon dioxide and heat from a fuel cell anode exhaust stream, is exclusively used as the inputs to a methanol production plant. The methanol production plant may also be powered exclusively by electricity produced by the fuel cell and any ORC units within the production plant. As such, the proceed described herein allows for the use of the cooled, condensed, separated, recovered, pressurized and reheated steam and carbon dioxide to mix at a stoichiometric ratio in an electric catalytic reformer powered by electricity produced in the fuel cell and ORC units to produce synthesis gas for conversion into methanol in a methanol synthesis reactor. As presented, this process allows for the production of methanol at near zero GHG emissions.

As discussed below, it will be understood that supplying the reactants and energy from a fuel cell enables this process to produce methanol at near zero GHG emissions, and generally at a higher efficiency, as electric heating is generally more efficient that the more commonly used gas combustion furnaces. Furthermore, the process may use any of the industry standard commercialized catalysts in both the synthesis gas catalytic reformer and the methanol synthesis reactor at any preferred pressures and temperatures, and this process may be applicable to any fuel cell exhaust stream that includes heat, carbon dioxide, and steam.

Figure 2:
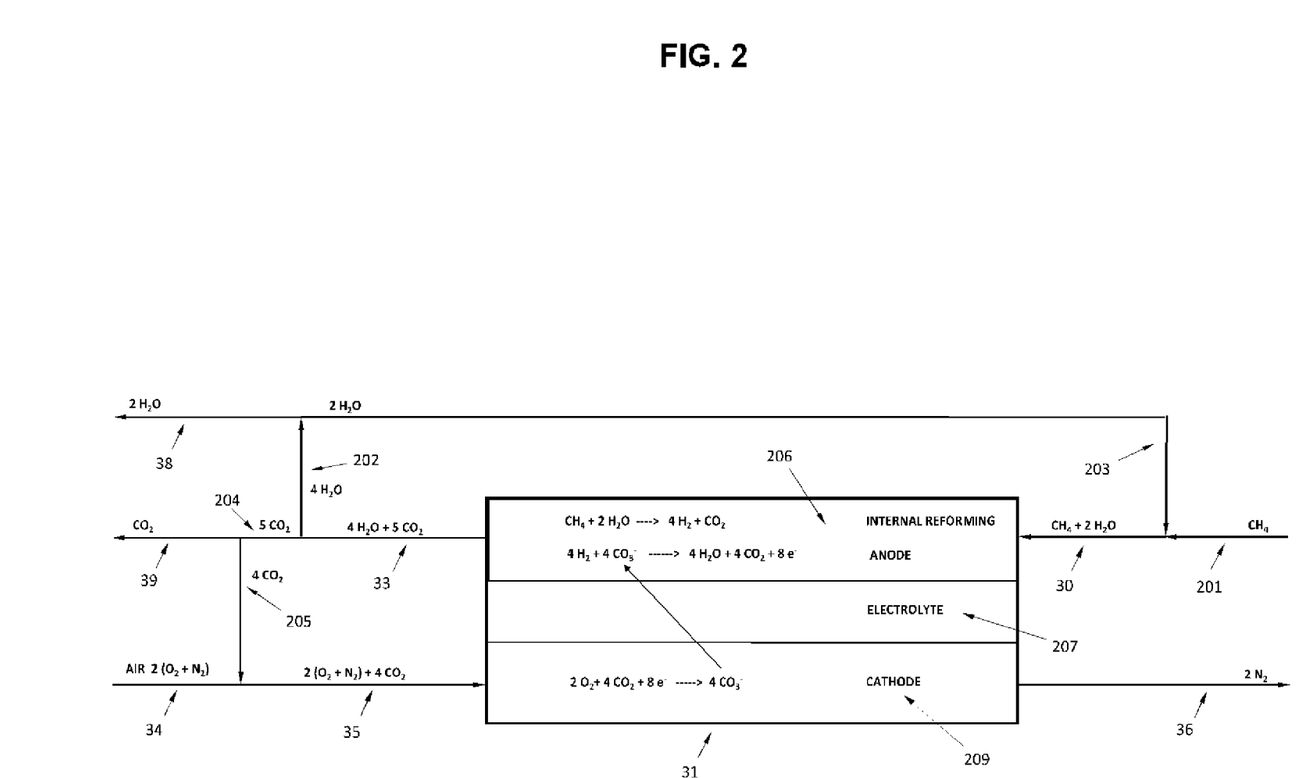
FIG. 2 depicts a stoichiometric balance of the flow streams in the GRU and the fuel cell.

Referring to FIG. 2, the stoichiometric balance of a fuel cell anode and cathode inlet and outlet streams prepared in a GRU 2 as shown in FIG. 1 will now be discussed.

In this example, a mole of natural gas in stream 201, shown as methane, is heated by stream 36 at the GRU 2 and mixed with 2 moles of steam in stream 203. The mixture enters anode 206 in fuel cell 31 through stream 30. At the anode 206, internal reforming converts the one mole of methane and 2 moles of water into 4 moles of hydrogen and 1 mole of carbon dioxide as per the following equation, $CH_4+2H_2O \rightarrow 4H_2+CO_2$. At the anode, the produced 4 moles of hydrogen react with 4 moles of carbonate ion to produce 4 moles of water, 4 moles of carbon dioxide and 8 electrons as per the following equation $4H_2+4CO_3^- \rightarrow 4H_2O+4CO_2+8e^-$. These high temperature products of reaction exit the anode as exhaust stream 33 of 4 moles of water and 5 moles of carbon dioxide. At the GRU 2, the anode exhaust stream 33 is cooled and the steam is condensed and separated from the carbon dioxide. The separated 4 moles of water stream 202 is split into streams 203 and 38. Two moles of water in stream 203 are pressurized and heated by heat exchange with stream 33 and heat exchange with stream 36 to produce steam that is added to methane stream 201 to feed anode 206 in fuel cell 31. The remaining two moles of water in stream 38 are pressurized and heated by heat exchange with stream 33 to produce steam and delivered to methanol unit as a reactant for the production of synthesis gas.

At the GRU 2, the separated 5 moles of carbon dioxide, stream 204, is further cooled, condensed and separated. The 4 moles of separated carbon dioxide gaseous stream 205, is heated and mixed with 2 moles of air, stream 34. The mixed air/carbon dioxide stream 35 is further heated at the GRU 2 and enters the cathode 209 in fuel cell 31. At the cathode 209, 4 moles of carbon dioxide reacts with 2 moles of oxygen in the mixture and 8 electrons to generate 4 moles of carbonate ions and as per the following equation: $2O_2+4CO_2+8e^- \rightarrow 4CO_3^-$. The generated 4 moles of carbonate ions are transferred through electrolyte 207 in fuel cell 31 to the anode 206 where the 4 moles of carbonate ions react with 4 moles of hydrogen produced at anode 206 to produce 4 moles of water, 4 moles of carbon dioxide and 8 electrons. The cooled, condensed, separated and recovered one mole of liquid carbon dioxide is pressurized and heated by heat exchange with stream 33 and delivered as stream 39 to the methanol unit as a reactant for the production of synthesis gas in an electric catalytic reformer. The 2 moles nitrogen in the cathode feed stream 35 exit the cathode exhaust stream 36 unreacted to the GRU 2 for heat recovery.

The above describes the stoichiometric balance of the steam stream 38, and carbon dioxide stream 39 exported from a fuel cell 31 through a GRU 2 to supply a methanol unit for the production of synthesis gas and conversion into methanol.

Figure 3:
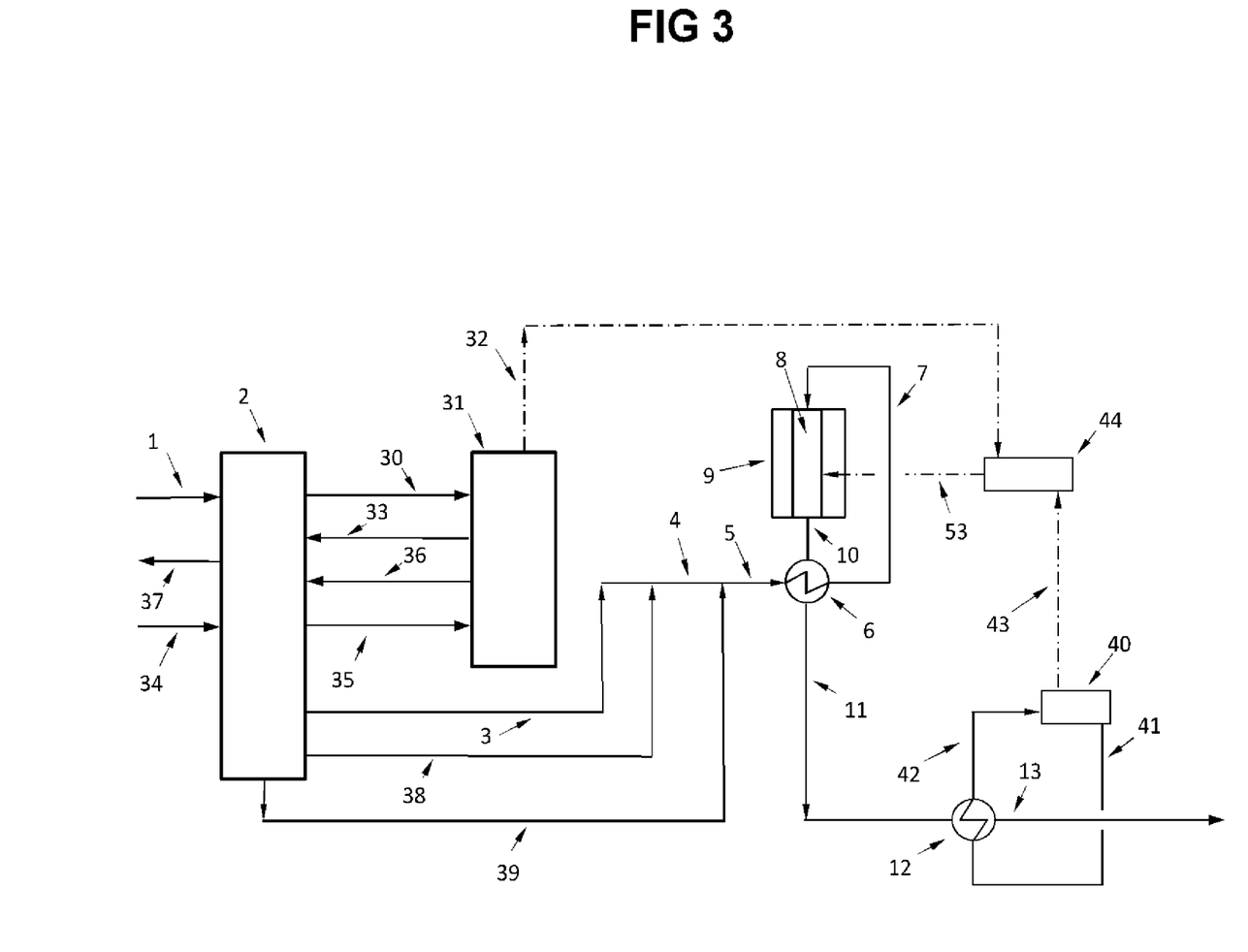
FIG. 3 is a process flow diagram that illustrates synthesis gas production at variable stoichiometric ratios for process applications other than methanol.

Referring to FIG. 3, a more general process flow diagram is shown without a methanol production plant. This demonstrates how a fuel cell may be integrated with catalytic reforming processes to deliver required stoichiometric ratios for the production of synthesis gases for reactions into products other than methanol. The main feature of the proposed process in FIG. 3 is the advantage of employing a natural gas fed fuel cell to provide carbon dioxide and steam as reactants to meet desirable hydrogen to carbon monoxide synthesis gas ratios and the electricity required for an electric catalytic reactor at near zero GHG emissions, assuming the stoichiometric ratio allows for the entire supply of exhausted carbon to be used. Other inputs, such as natural gas and water/steam, may be adjusted to ensure the exhausted carbon is used to minimize GHG emissions.

As per FIG. 3, the steam stream 38 may be added to natural gas stream 3 at desired stoichiometric ratios as well as carbon dioxide stream 39 addition to stream 4 at desired stoichiometric ratios to produce a synthesis gas stream 10 at a desirable ratios of hydrogen to carbon monoxide for the reaction into products other than methanol. It is understood different catalysts and operating conditions may be employed to meet desired outcomes, and those skilled in the art will be able to design appropriate controls to ensure these conditions are met.

In this patent document, the word "comprising" is used in its non-limiting sense to mean that items following the word are included, but items not specifically mentioned are not excluded. A reference to an element by the indefinite article "a" does not exclude the possibility that more than one of the elements are present, unless the context clearly requires that there be one and only one of the elements.

The scope of the claims should not be limited by the preferred embodiments set forth in the examples, but should be given a broad purposive interpretation consistent with the description as a whole.

What is claimed is:

1. A method of producing synthesis gas using a fuel cell having an anode and a cathode, a Gas Recovery Unit (GRU), and an electric catalytic reformer, the method comprising the steps of:

operating the fuel cell to generate electricity and an exhaust stream comprising steam and carbon dioxide, the fuel cell being connected to a power distributor;

using the GRU, conditioning and separating the exhaust stream to produce streams of steam and carbon dioxide;

producing a reformer input stream by combining a stream of methane, the stream of carbon dioxide, and the stream of steam according to a stoichiometric ratio required to produce a stream of synthesis gas;

reacting the reformer input stream in the electric catalytic reformer to produce the stream of synthesis gas, the electric catalytic reformer being powered by the power distributor; and using a power generator, recovering heat from the stream of synthesis gas to produce electricity, the power generator being connected to the power distributor.

2. The method of claim 1, wherein the stream of synthesis gas is reacted in a synthesis reactor to produce a petrochemical.

3. The method of claim 2, wherein heat is recovered from the synthesis reactor using a Rankine Cycle or an Organic Rankine Cycle power generator that is connected to the power distributor.

4. The method of claim 1, wherein the GRU receives a natural gas stream, the GRU conditioning a first portion of the natural gas stream as a fuel gas stream to feed the fuel cell anode, and conditioning a second portion of the natural gas stream as the stream of methane.

5. The method of claim 4, wherein the GRU further conditions a fuel stream of steam that is mixed with the fuel gas stream to feed the anode of the fuel cell.

6. The method of claim 1, wherein the stoichiometric ratio of methane, carbon dioxide, and steam is 3:1:2.

7. The method of claim 6, further comprising the step of reacting the synthesis gas in a methanol synthesis reactor to produce methanol.

8. The method of claim 7, further comprising the step of recovering heat from the methanol synthesis reactor using a power generator to produce electricity, the reactor power generator being connected to the power distributor.

9. The method of claim 8, wherein the power generator is a Rankine Cycle or an Organic Rankine Cycle power generator.

10. The method of claim 1, wherein the fuel cell is operated to produce a desired amount of steam and carbon dioxide, and any excess electricity is sold to a third-party consumer.

11. A system for producing hydrocarbon-based products, comprising:

a power distributor;

a fuel cell having an anode and a cathode, the fuel cell generating electricity and an exhaust stream comprising steam and carbon dioxide, the power distributor receiving electricity from the fuel cell;

a Gas Recovery Unit (GRU) connected to the fuel cell, the GRU being adapted to:

condition an input stream of natural gas to produce a first methane stream and a second methane stream, the first methane stream comprising fuel gas for the fuel cell;

condition the exhaust stream from the fuel cell to produce a stream of steam and a stream of carbon dioxide; and control an output of the second methane stream, the stream of steam and the stream of carbon dioxide according to a stoichiometric ratio;

an electric catalytic reformer that receives the second methane stream, the stream of steam, and the stream of carbon dioxide, the electric catalytic reformer being powered by electricity from the power distributor to produce a stream of synthesis gas; and a power generator that recovers heat from the stream of synthesis gas to produce electricity, the power generator being connected to the power distributor.

12. The system of claim 11, further comprising a synthesis reactor that reacts the stream of synthesis gas to produce a petrochemical in an exothermic reaction.

13. The system of claim 12, further comprising a power generator comprises a Rankine Cycle or an Organic Rankine Cycle that generates electricity from heat produced by the synthesis reactor, the power generator being connected to the power distributor.

14. The system of claim 12, wherein the stoichiometric ratio of methane, carbon dioxide and steam is 3:1:2, and the synthesis reactor is adapted to produce methanol.

15. The system of claim 11, wherein the GRU is adapted to mix a portion of steam obtained from the exhaust stream with the first methane stream as a fuel stream for the anode of the fuel cell.

16. The system of claim 11, wherein fuel cell is adapted to operate the power distributor is adapted to supply excess electricity to a third party consumer, the excess electricity being generated fuel cell is operated to produce a desired amount of steam and carbon dioxide, and any excess electricity is sold to a third-party consumer.

* * * * *